United States Patent [19]

Phillips et al.

[11] 3,959,330

[45] May 25, 1976

[54] SUBSTITUTED DICHLOROMETHYL THIOCYANATES AND THEIR MANUFACTURE

[75] Inventors: Wendell Gary Phillips, Olivette; Kenneth Wayne Ratts, Creve Coeur, both of Mo.

[73] Assignee: Monsanto Company, St. Louis, Mo.

[22] Filed: Nov. 8, 1971

[21] Appl. No.: 196,739

[52] U.S. Cl. ............................. 260/454; 71/88; 71/94; 71/95; 71/104; 260/239 B; 260/293.85; 260/326.82; 260/453 R; 424/244; 424/267; 424/274; 424/302
[51] Int. Cl.² ................................. C07C 161/02
[58] Field of Search .............. 71/104, 118, 111; 260/454, 453 R

[56] References Cited
UNITED STATES PATENTS

| | | | |
|---|---|---|---|
| 2,419,888 | 4/1947 | Nolan et al. | 260/454 |
| 2,572,564 | 10/1951 | Himel et al. | 260/454 |
| 2,863,752 | 12/1958 | Hamm et al. | 71/118 |
| 2,973,258 | 2/1961 | Hamm et al. | 71/118 |
| 3,404,172 | 10/1968 | Tomalia | 260/454 |
| 3,530,181 | 9/1970 | Soloway et al. | 71/118 |
| 3,557,210 | 1/1971 | Hamm et al. | 71/118 |
| 3,557,211 | 1/1971 | Rumanowski | 71/118 |
| 3,637,847 | 1/1972 | Olin | 71/118 |
| 3,694,435 | 9/1972 | Phillips | 260/543 H |

OTHER PUBLICATIONS

Badische Aniline, "Herbicidal thiocyanoacetanilides" (1970), CA 73, No. 45106n, (1970).
Tsybol'skaya et al., "Herb. activity of some aromatic ders, etc." (1964), CA 61, p. 2411, (1964).

*Primary Examiner*—Glennon H. Hollrah
*Attorney, Agent, or Firm*—William I. Andress

[57] ABSTRACT

Substituted dichloromethyl thiocyanates are prepared from substituted dichloromethane sulfenyl chlorides by reaction with an ionized cyanide in the presence of water and an immiscible organic solvent. These compounds are pesticidally active and particularly useful as herbicides.

7 Claims, No Drawings

SUBSTITUTED DICHLOROMETHYL THIOCYANATES AND THEIR MANUFACTURE

This invention relates to substituted dichloromethyl thiocyanates of the formula $$E-CCl_2-S-CN$$

and their manufacture from the corresponding substituted dichloromethane sulfenyl chlorides of the formula $$E-CCl_2-S-Cl$$

and an ionized cyanide of the formula $$M^+CN^-$$

wherein E— is —CN, $$-\overset{O}{\underset{O}{\overset{\|}{S}}}-X, \quad -\overset{O}{\overset{\|}{C}}-X, \quad -\overset{O}{\overset{\|}{C}}-O-Y, \text{ and } -\overset{O}{\overset{\|}{C}}-N\overset{R'}{\underset{R}{\diagdown}},$$

X is phenyl or substituted phenyl, Y is lower alkyl or benzyl, R is phenyl, substituted phenyl, lower alkyl, lower alkoxyalkyl, or lower alkoxy, R' is phenyl, substituted phenyl, or lower alkyl, or R and R' when taken together are alkylene of the empirical formula $C_nH_{2n}$ wherein $n$ is an integer from 4 through 8, inclusive, and having from 4 through 8 carbons in a continuous chain between the nitrogen terminal valence bonds, and M is an alkali metal or hydrogen.

As employed herein, the term "substituted phenyl" designates phenyl groups of the formula $$-\underset{\phantom{X}}{\bigcirc}-Z_m$$

wherein Z is halo, trihalomethyl, cyano, nitro, lower alkyl or lower alkoxy, and $m$ is an integer from 1 through 3 inclusive, provided that when Z is nitro, $m$ cannot exceed 2. The term "halo" designates a halogen atom selected from fluorine, chlorine, bromine and iodine.

As employed herein, the terms "lower alkyl" and "lower alkoxy" designate those groups wherein the aliphatic chain is straight or branched and has from 1 through 5 carbons inclusive. As employed herein, the term "lower alkoxyalkyl" designates those groups wherein the aliphatic chains are straight or branched and contain a combined total of from 2 through 8 carbons inclusive.

Examples of heterocyclic groups of nitrogen and alkylene of the empirical formula $C_nH_{2n}$ wherein $n$ is an integer from 4 through 8, inclusive, and having from 4 through 8 carbons in a continuous chain between the nitrogen terminal valence bonds include but are not limited to pyrrolidinyl, piperidinyl, hexamethyleneimino, heptamethyleneimino, octamethyleneimino, 2-ethylpyrrolidinyl, 3-butylpyrrolidinyl, 2,5-dimethylpyrrolidinyl, 2,5-diethylpyrrolidinyl, 3,4-dimethylpyrrolidinyl, 2-pipecolinyl, 3-pipecolinyl 4-pipecolinyl, 2,6-dimethylpiperidinyl, 2-ethyl-6-methylpiperidinyl, 2-propylpiperidinyl, 3-methylhexamethyleneimino, 3,4-dimethylhexamethyleneimino, and the various isomeric forms thereof.

Alkali metals are metals of Group I of the Periodic Table. Preferred alkali metals are lithium, sodium and potassium, more preferred are sodium and potassium.

The compounds of this invention are conveniently and efficiently prepared by the reaction, in the presence of water and an immiscible organic solvent, of about equimolecular proportions of a substituted dichloromethane sulfenyl chloride of the formula $$E-CCl_2-S-Cl$$

and an ionized cyanide of the formula $$M^+CN^-$$

wherein E and M have the aforementioned significance. The reaction is postulated to proceed as follows:

$$ECCl_2SCl + M^+CN^- \rightarrow ECCl_2S-CN + M^+Cl^-.$$

When M is hydrogen the reaction mass must additionally contain an HCl scavenger. The HCl scavenger must be present in at least an equimolecular amount as compared to the substituted sulfenyl chloride. Generally not more than twice the equimolecular amount of scavenger is useful although the maximum amount is not critical. The type of scavenger is not critical to the invention so long as it does not interfere with the reaction of the cyanide and the substituted sulfenyl chloride. Preferred scavengers are trialkyl amines. More preferred trialkyl amines have from 2 through 5 carbons in the alkyl group.

The reaction mass is a two phase system, an aqueous or water phase and an organic solvent phase. Examples of organic solvents, i.e., common organic liquids which are immiscible with water and inert under the reaction conditions and which dissolve the sulfenyl chloride and the desired product of the reaction, include, but are not limited to, aliphatic hydrocarbons, such as pentane, hexane, mineral spirits, etc., aromatics such as benzene, toluene, xylenes, etc., ethers such as diethyl ether, diisopropyl ether, petroleum ether, etc., esters such as methyl acetate, ethyl acetate, propyl acetate, etc., and other inert organics which are solvents for the sulfenyl chloride. The ionized cyanide and the chloride salt by-product are generally not soluble in the above organic solvents. Accordingly, the reaction between the sulfenyl chloride and the ionized cyanide takes place at the interface of the two phase system.

Although the reaction can proceed without agitation, agitation of the reaction mass facilitates the reaction by providing intimate association of the two phases. Thus, agitation of the reaction mass is preferred in the method of this invention.

It is likewise preferred to have the ionized cyanide present in excess of one molecular proportion of sulfenyl chloride in order to minimize reaction time. It is more preferred to have the ionized cyanide present in an excess in the amount of from about 3 to about 10 molecular proportions per molecular proportion of sulfenyl chloride.

The reaction is normally carried out at a temperature above the freezing point of the system but preferably not above its boiling point. More preferably, the reaction is carried out at temperatures of from about 0 degrees Centigrade (°C.), to about 60°C. The reaction is most conveniently carried out at about room temperature, about 23°C., with rapid agitation. The reaction is usually carried out at atmospheric pressure, but higher or lower pressures may be utilized if equipment and other factors favor such higher or lower pressures. The reaction may be carried out in an open vessel as well as under reflux.

Substituted dichloromethyl thiocyanates of this invention are useful as biocides. Exemplary of such biocidal uses for these products is the control of nematodes, arachnids, arthropods and insects as well as eradication of noxious weeds. These compounds are particularly useful as herbicides.

Herbicidal compounds are useful in the selective killing of weeds in crops. In using the compounds of the present invention as pre-emergent and contact herbicides, the compounds can be used alone or in combination with a material referred to in the art as an adjuvant in liquid or solid form. Herbicidal formulations are prepared by admixing the compound which is the active ingredient of the formulation with an adjuvant including diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The herbicidal formulations usually contain from about 0.01 percent to about 99 percent by weight of the active ingredient. Application of these formulations to the soil or growth media can be carried out by simply admixing with the soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above ground portions of plants can be carried out by conventional methods, e.g. power dusters, boom and hand sprayers and spray dusters. The formulations can also be applied from airplanes as a dust or a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

The exact amount of active ingredient to be employed is dependent upon the response desired in the plant as well as such other factors as the plant species and stage of development thereof, the specific soil and depth at which the active ingredients are distributed in the soil and the amount of rainfall as well as the specific active ingredient employed. In foliar treatment, the active ingredients are applied in amounts from about 1 to about 50 or more pounds per acre. In applications to soil for the control of the growth of germinant seeds, germinative seeds, emerging seedlings and established vegetation, the active ingredients are applied in amounts from about 0.1 to about 25 or more pounds per acre. It is believed that one skilled in the art can readily determine from the teachings of this specification the general procedure for any application.

Manufacture of substituted dichloromethane sulfenyl chlorides, used as starting materials in the preparation of the compounds of the present invention, is taught in prior U.S. patent applications Ser. Nos. 139,976 and 139,978 filed May 3, 1971, and each entitled "Substituted Alpha, Alpha-Dichloro-Methane Sulfenyl Chlorides and Their Manufacture."

Ionized cyanides used in the preparation of the compounds of the present invention are known compounds.

As illustrative of this invention, but not limitative thereof, is the following.

EXAMPLE 1

To a suitable reaction vessel equipped with an agitator is charged approximately 100 milliliters (ml.) of dichloromethane. Approximately 10 grams (g.), about 0.03 moles, of 2-(chlorothio)-2,2-dichloro-N-isopropylacetanilide are dissolved in the dichloromethane. Approximately 10 g. of potassium cyanide, about 0.15 moles, is dissolved in about 100 ml. of water. This solution is then added to the reaction mass. The mass is stirred for about 36 hours at ambient room temperature. The dichloromethane evaporates during this agitation period leaving a solid suspended in the water. This solid is separated from the aqueous portion by filtration. Having determined that the reaction is incomplete, the residue is redissolved in about 100 ml. of dichloromethane. An additional 25 g., about 0.4 moles, of potassium cyanide is dissolved in about 200 ml. of water and added to the dichloromethane solution. The mass is stirred overnight at ambient room temperature. Thereafter the aqueous portion is removed by filtration and the residual solid is recrystallized twice from petroleum ether. The white solid is found to have a melting point of about 122° to 124°C. and is identified by nuclear magnetic resonance and infrared analysis as 2,2-dichloro-N-isopropyl-2-thiocyanatoacetanilide.

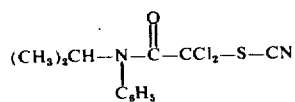

Calculated for $C_{12}H_{12}Cl_2N_2OS$: C, 47.53; H, 3.96; N, 9.24. Found: C, 47.43; H, 3.75; N, 9.13.

EXAMPLES 2 THROUGH 32

The procedure of Example 1 is followed except that, in place of about 10 g. 2-(chlorothio)-2,2-dichloro-N-isopropylacetanilide, an approximately equimolecular amount of the compound of Column A is charged and the product of Column B is obtained:

| Example | A | B |
|---|---|---|
| 2 | | |

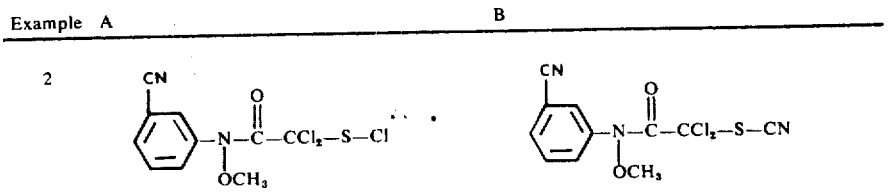

| Example | A | B |
|---|---|---|
| 3 | $(C_6H_5)_2N-\overset{O}{\underset{\|}{C}}-CCl_2-S-Cl$ | $(C_6H_5)_2N-\overset{O}{\underset{\|}{C}}-CCl_2-S-CN$ |
| 4 | $(CH_3)_3C-\underset{\underset{\text{Cl}}{\underset{\|}{C_6H_3}}}{N}-\overset{O}{\underset{\|}{C}}-CCl_2-S-Cl$ (3,4-diCl-phenyl) | $(CH_3)_3C-\underset{\underset{\text{Cl}}{\underset{\|}{C_6H_3}}}{N}-\overset{O}{\underset{\|}{C}}-CCl_2-S-CN$ (3,4-diCl-phenyl) |
| 5 | $C_6H_5-\overset{O}{\underset{\underset{O}{\|}}{S}}-CCl_2-S-Cl$ | $C_6H_5-\overset{O}{\underset{\underset{O}{\|}}{S}}-CCl_2-S-CN$ |
| 6 | 2,6-diethylphenyl-N(CH$_2$OCH$_3$)-CO-CCl$_2$-S-Cl | 2,6-diethylphenyl-N(CH$_2$OCH$_3$)-CO-CCl$_2$-S-CN |
| 7 | $CH_3O-\underset{\underset{C_6H_5}{\|}}{N}-\overset{O}{\underset{\|}{C}}-CCl_2-S-Cl$ | $CH_3O-\underset{\underset{C_6H_5}{\|}}{N}-\overset{O}{\underset{\|}{C}}-CCl_2-S-CN$ |
| 8 | $CH_3(CH_2)_4O-\underset{\underset{CH_3}{\|}}{N}-\overset{O}{\underset{\|}{C}}-CCl_2-S-Cl$ | $CH_3(CH_2)_4O-\underset{\underset{CH_3}{\|}}{N}-\overset{O}{\underset{\|}{C}}-CCl_2-S-CN$ |
| 9 | $(CH_3)_2CHO-\underset{\underset{C_2H_5}{\|}}{N}-\overset{O}{\underset{\|}{C}}-CCl_2-S-Cl$ | $(CH_3)_2CHO-\underset{\underset{C_2H_5}{\|}}{N}-\overset{O}{\underset{\|}{C}}-CCl_2-S-CN$ |
| 10 | 2,4-dicyanophenyl-N(CH$_3$)-CO-CCl$_2$-S-Cl | 2,4-dicyanophenyl-N(CH$_3$)-CO-CCl$_2$-S-CN |
| 11 | $\underset{\underset{CH_3}{\|}}{N}(C_2H_4OCH_2CH_3)-\overset{O}{\underset{\|}{C}}-CCl_2-S-Cl$ | $\underset{\underset{CH_3}{\|}}{N}(C_2H_4OCH_2CH_3)-\overset{O}{\underset{\|}{C}}-CCl_2-S-CN$ |
| 12 | 2,6-diiodophenyl-N(C$_6$H$_5$)-CO-CCl$_2$-S-Cl | 2,6-diiodophenyl-N(C$_6$H$_5$)-CO-CCl$_2$-S-CN |
| 13 | 3-methylphenyl-N[(CH$_3$)$_2$CH(CH$_2$)$_4$]-CO-CCl$_2$-S-Cl | 3-methylphenyl-N[(CH$_3$)$_2$CH(CH$_2$)$_4$]-CO-CCl$_2$-S-CN |
| 14 | NC-CCl$_2$-S-Cl | NC-CCl$_2$-S-CN |

| Example | A | B |
|---|---|---|
| 15 | 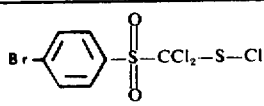 | 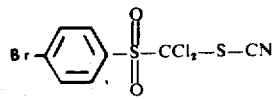 |
| 16 | 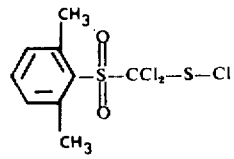 | 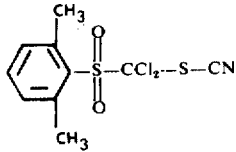 |
| 17 | 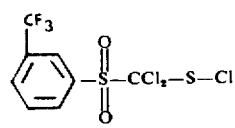 | 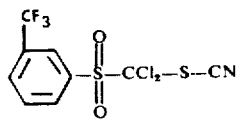 |
| 18 | 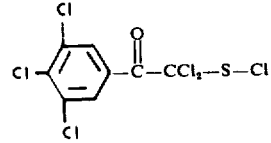 | 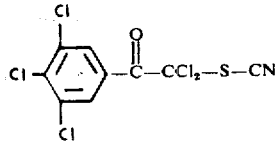 |
| 19 |  | 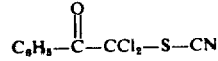 |
| 20 | 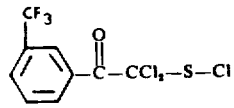 | 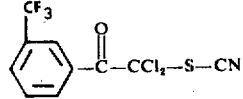 |
| 21 | 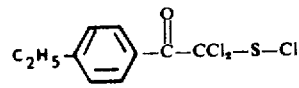 | 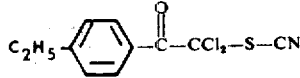 |
| 22 | 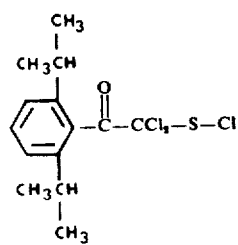 | 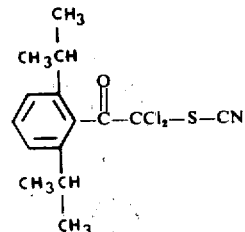 |
| 23 | 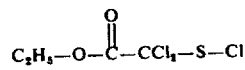 | 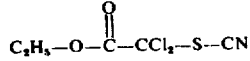 |
| 24 | 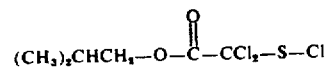 | 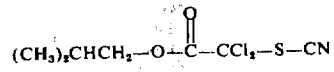 |
| 25 | 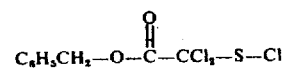 | 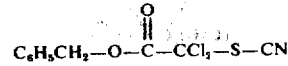 |
| 26 | 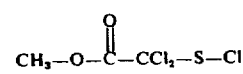 | 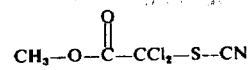 |

| Example | A | B |
|---|---|---|
| 27 | 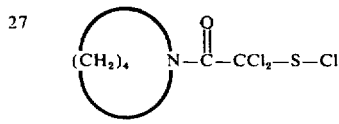 | 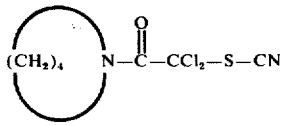 |
| 28 | 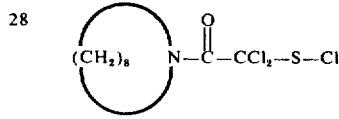 | 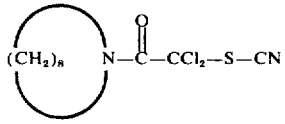 |
| 29 | 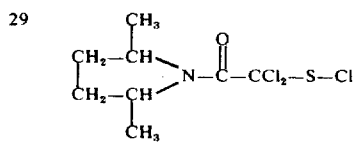 | 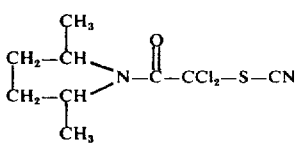 |
| 30 | 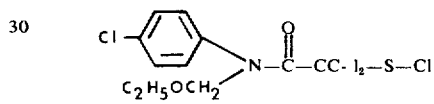 | 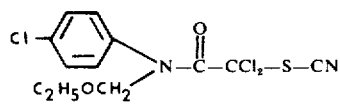 |
| 31 | 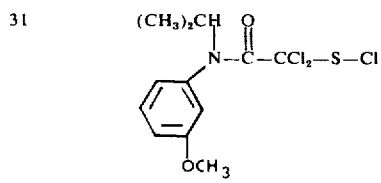 | 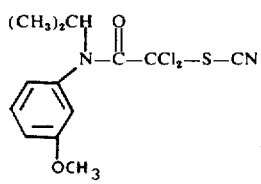 |
| 32 | 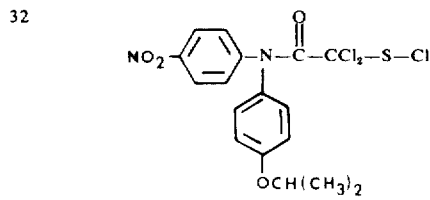 | 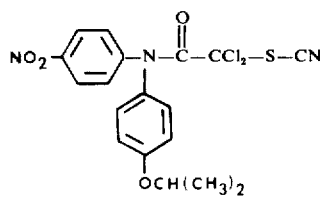 |

EXAMPLE 33

The procedure of Example 1 is followed except that, in place of about 35 g. of potassium cyanide, an approximately equimolecular amount of sodium cyanide is charged and the product of Example 1 is obtained.

EXAMPLES 34 AND 35

The procedure of Example 1 is followed except that the reaction vessel is a closed vessel, in place of potassium cyanide an equimolecular amount of hydrogen cyanide is added and, in addition, about 0.06 moles of the specified trialkyl amine is added immediately to the sulfenyl chloride. The product of Example 1 is obtained.

Example 34 — Triethyl amine.
Example 35 — Tributyl amine.

EXAMPLE 36

Contact herbicidal activity of representative substituted S-dichloromethyl organothiocyanates of this invention is determined by the following procedure:

The compound to be tested is applied in spray form to plants of a given age of several grasses and broadleaf species. After the plants are the desired age, each aluminum pan of plants is sprayed with a given volume of a 0.2% concentration solution of the candidate chemical, corresponding to a rate of approximately 3.6 lbs. per acre. This solution is prepared from an aliquot of a 2% solution of the candidate compound in acetone, a known amount of cyclohexanone-emulsifying agent mix, and sufficient water to make up to volume. The emulsifying agent is a mixture comprising 35 wt. percent of a tall oil-ethylene oxide condensate having about 6 moles of ethylene oxide per mole of tall oil. The injuries to the plants are then observed approximately 14 days later and the results are recorded.

Contact herbicidal activity of the compound prepared in Example 1 is observed against Johnson grass and downy brome.

While this invention has been described with respect to certain embodiments it is to be understood that it is not so limited and that variations and modifications thereof obvious to those skilled in the art to which this

What is claimed is:
1. A compound of the formula

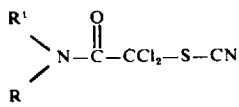

wherein R is lower alkyl, lower alkoxyalkyl, lower alkoxy, phenyl or substituted phenyl of the formula

wherein Z is halo, trihalomethyl, cyano, nitro, lower alkyl or lower alkoxy, and $m$ is an integer from 1 through 3 inclusive, provided that when Z is nitro, $m$ cannot exceed 2 and $R^1$ is phenyl or substituted phenyl of the formula

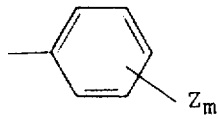

wherein Z and $m$ have the aforementioned significance.
2. A compound of claim 1 wherein R is lower alkyl.
3. A compound of the formula

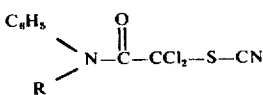

wherein R is lower alkyl.
4. The compound of claim 3 wherein R is isopropyl.
5. A compound of claim 1 wherein R is lower alkoxy.
6. A compound of claim 1 wherein $R^1$ is halophenyl.
7. A compound of claim 1 wherein R is lower alkoxyalkyl.

* * * * *